United States Patent [19]

Engl et al.

[11] 4,188,386

[45] Feb. 12, 1980

[54] COMPOSITIONS CONTAINING THIOCYANIC ACID AND HEXAMETHYLENE-TETRAMINE, PRODUCTION PROCESS AND ADMINISTRATION THEREOF AS BACTERICIDE AND MYCOCIDE

[75] Inventors: Robert Engl, Wasserburg; Hans Richter, Reitmehring, both of Fed. Rep. of Germany

[73] Assignee: Meggle Milchindustrie GmbH & Co. KG, Reitmehring, Fed. Rep. of Germany

[21] Appl. No.: 849,262

[22] Filed: Nov. 7, 1977

[51] Int. Cl.$^2$ ............................................. A61K 31/53
[52] U.S. Cl. ..................................... 424/249; 544/186
[58] Field of Search ................ 544/185, 186; 424/249, 424/302

[56] References Cited

U.S. PATENT DOCUMENTS

| 2,647,897 | 8/1953 | Weidner | 544/186 |
| 2,912,435 | 11/1959 | Scholz | 544/185 |
| 3,936,451 | 2/1976 | Orem et al. | 424/249 |

OTHER PUBLICATIONS

Chemical Abstracts, vol. 81 (1974), p. 115885g.

*Primary Examiner*—V. D. Turner
*Attorney, Agent, or Firm*—Kenyon & Kenyon

[57] ABSTRACT

Disclosed herein is a process for producing dry compositions containing thiocyanic acid and hexamethylene-tetramine wherein hexamethylene-tetramine is reacted with an alkali or alkaline earth metal thiocyanate in the aqueous phase in the presence of acid, and wherein the aqueous reaction product solution, without isolation of the reaction product, is combined with an inert carrier substance and dried.

15 Claims, No Drawings

COMPOSITIONS CONTAINING THIOCYANIC ACID AND HEXAMETHYLENE-TETRAMINE, PRODUCTION PROCESS AND ADMINISTRATION THEREOF AS BACTERICIDE AND MYCOCIDE

BACKGROUND OF THE INVENTION

Hexamethylene-tetramine thiocyanate has been used for a long time for combatting bacterial infections in veterinary medicine. It has been also known as having high antimycotic activity and being apt for preventing and diminishing yeasts and moulds in animal feed. (See DT-OS No. 22 43 982)

Hexamethylene-tetramine-thiocyanate is formed when concentrated aqueous solutions of hexamethylenetetramine are combined with equimolar amounts of thiocyanic acid. One way of production consists of combining hexamethylenetetramine, ammoniumthiocyanate and hydrochloric acid.

However, thiocyanic acid is not stable in aqueous solution, showing decomposition already at concentrations of 6% and above. Moreover, hexamethylenetetramine-thiocyanate splits off ammonium-ions under the influence of heat in aqueous solution or by influence of high humidity.

In order to overcome these disadvantages, according to DT-PS No. 812 912, hexamethylenetetramine, ammonium-thiocyanate and sulfuric acid are reacted in organic solvents, e.g., methanol or ethanol, whereby a stable mixture of hexamethylenetetramine-thiocyanate and ammoniumsulfate is obtained. The stabilizing influence of ammoniumsulfate can even be observed in aqueous phase (see DT-PS No. 860 052). A stable salt complex of the formula $(C_6H_{12}N_4.HSCN)_2.(NH_4)_2SO_4$ is formed.

A variation of above mentioned process consists, according to DT-PS No. 881 041, in substituting an alkaline earth metal thiocyanate for ammoniumthiocyanate, whereby an insoluble alkaline earth sulfate is obtained and removed from the mixture. The clear filtrate is then stabilized by adding hexamethylene-tetramine, thereby increasing the pH-value, and may be administered directly in this form for injections.

However, utilization of aqueous solutions containing hexamethylene-tetramine-thiocyanate is impaired by the fact, that the product decomposes when evaporized and dried, under formation of ammonium salts. Pure products are obtained only with the aid of alkanoles as precipitating agents at low temperatures.

In practice it has been therefore necessary to isolate hexamethylene-tetramine-thiocyanate as a complex salt, together with ammoniumsulfate or ammoniumphosphate. Products thus obtained are nevertheless not very stable and readily form lumps during storage and exposure to air due to their hygroscopic properties.

SUMMARY OF THE INVENTION

It is the object of this invention to provide an improved process for the production of compositions containing thiocyanic acid and hexamethylene-tetramine, which do not decompose during long time storage and do not form lumps at high humidities.

Another object of this invention is to provide compositions containing thiocyanic acid and hexamethylene-tetramine and having the aforesaid good properties.

Surprisingly it was found, that reaction solutions containing hexamethylene-tetramine, thiocyanates and an acid can be dried without significant decomposition in the presence of carrier substances.

The scope of this invention is therefor a process for the production of compositions containing thiocyanic acid and hexamethylenetetramine whereby hexamethylenetetramine is reacted with thiocyanates in aqueous phase in presence of an acid, characterized by the fact, that the aqueous solution obtained is combined without isolation of the reaction product with a carrier substance and dried.

DETAILED DESCRIPTION OF THE INVENTION

Desiccation is achieved preferably by the spray drying process, according to this invention, but also application of the roller drying process is possible. Applying the spray drying process, air inlet temperature is commonly 150°–220° Centrigrades, air outlet temperature ranges from 50° Centigrade to the boiling point of water in the reaction solution, preferably 80° Centigrades.

Carrier substances as applied in the process of this invention are those which are physiologically harmless, which can absorb moisture without showing significant structural changes, and which are essentially inert with respect to hexamethylene-tetramine thiocyanates and the acid applied.

Examples for carrier substances are given below: Polysaccharides, e.g., genuine starch, microcrystalline cellulose, derivatives of cellulose e.g., carboxymethylcellulose, carboxycellulose and salts thereof; dry products from milk, e.g., skim milk powder; dry products from whey and whey derivatives, e.g., rennet cheese whey powder and acid whey powder; casein, caseinates and lactose. The dry products from milk or whey, lactose, casein and caseinates can be added in dry state or as concentrated solutions or dispersions to the reaction mixture. Furthermore, physiologically harmless carriers of inorganic origin, like silicic acid, silica, bentonite and aluminium-hydroxide may be used. The carrier substance amounts from 10 to 60%, preferably from 30 to 50%, based on the final product of the invention.

In addition to the carrier substances other additives like mineral salts, vitamins, essential components, flavourants a.s.o. may be admixed to the reaction solution or the dried product.

The alkali and alkaline earth metal thiocyante used in this invention is preferably sodium, potassium, ammonium, magnesium and calcium thiocyanate.

The term "acid" as used in this invention means mineral acids like hydrochloric acid, sulfuric acid and phosphoric acid, or organic acids like lactic acid, formic acid, citric acid, acetic acid or propionic acid. Phosphoric acid is preferred among inorganic acids. Whey acidified by aid of cation exchange resins in the acid form or acidified whey derivatives also serve as organic acid component.

Examples of such whey derivatives are whey concentrates, delactosed whey concentrates and permeates resulting from membrane filtration processes.

The molar ratio of hexamethylenetetramine as compared to alkali or alkaline earth metal thiocyanate is usually 0.8:1 to 1.5:1, preferably 1:1 to 1,2:1.

The equivalent ratio of acid as compared to alkali or alkaline earth thiocyanate is usually 0.9:1 to 1.1:1, preferably 1:1. The pH of the reaction mixture shall not fall below 5.

It is possible to use the genuine acids of milk. For this purpose concentrates from acid whey or partially delactosed acid whey are treated with cation exchange to remove cations, thus liberating hydrochloric, phosphoric, citric and lactic acid originally present in the milk derivative as salts.

It is the main advantage of the process of this invention, that utilization of the reaction product hexamethylenetetramine-thiocyanate is possible without laborous isolation technique as necessary when applying usual production techniques. Moreover, decomposition of hexamethylenetetramine-thiocyanate is insignificant during the drying process. Obviously the carrier substance acts as a stabilizer.

The products obtained by the invention are stable during storage and establish high antimicrobial activity.

The compositions obtained by the inventive process can be directly used as bactericides and mycocides, e.g., as additives to animal feed. The following examples illustrate the invention but do not constitute a restriction thereof:

EXAMPLE 1

Preparation of a dry product from hexamethylenetetramine, potassium thiocyanate, phosphoric acid and starch: 100 kg hexamethylenetetramine and 69,3 kg of potassium thiocyanate are added to 715 kg of water in a stirring vessel and agitated to complete solution. 35 kg phosphoric acid (85%) are added slowly under continuous agitation taking care to prevent pH from falling below 5 for more than insignificant time. Stirring is continued until pH is at a stable level between 5 and 6. The solution should be kept under 30° Centigrades during the process, optionally by cooling, if necessary. 178,6 kg genuine starch are added and the viscous liquid is spray dried. A plain white powder is obtained having a SCN-content of 11.4%.

EXAMPLE 2

Preparation of a dry product as described in example 1, substituting sulfuric acid for phosphoric acid: An equivalent amount of half concentrated sulfuric acid is added instead of phosphoric acid. Spray drying results in a white powder as in example 1.

EXAMPLE 3

Comparison of a commercial composition of hexamethylenetetramine-thiocyanate with a composition obtained as described in example 1, with respect to storage stability: The samples were stored under 80% and 60% relative humidity, respectively. The commercial sample turned to a sticky and moist mass after 1 week at 80% r.h., at 60% r.h. the product showed forming of lumps. The product of the invention showed only slight lumpiness, the lumps being easily broken under light pressure. At 60% r.h. no lumps were observed.

The same comparative study was undertaken using sealed polyethylene sachets. The commercial product turned to hard lumps on exposure to 80% r.h., while the product of the invention only showed easily destroyable lumps.

EXAMPLE 4

Measurement of ammonia: A sample of preparation obtained according to example 1, having a pH of 5.4 is dissolved and an excess of magnesium oxide is added. Ammonia is expelled by bubbling air through the solution. The air is led through an acid trap and the residual acid is titrated. Ammonia content of sample (% of total N based on hexamethylenetetramine): 2.5%, 1,5%, 1.6%, 1.6%.

A sample which was previously heated for 30 minutes in solution to 90° Centigrade yielded under the conditions described above 3.4% of total N. Hexamethylene itself showed 0.4% of total N under the same test conditions. It can be concluded that only insignificant decomposition of the hexamethylenetetramine moiety had occurred during the production process.

What is claimed is:

1. A dry stable bactericidal and mycocidal composition comprised of (1) the unisolated reaction product of hexamethylenetetramine with an alkali or alkaline earth metal thiocyanate in the aqueous phase in the presence of acid and (2) a physiologically harmless carrier substance substantially inert towards the reaction compounds and the products thereof; wherein said composition is prepared by a process comprising:
   (a) reacting hexamethylenetetramine with an alkali or alkaline earth metal thiocyanate in the aqueous phase in the presence of acid;
   (b) combining the aqueous solution product obtained in said reaction, without isolation of reaction product, with a physiologically harmless carrier substance substantially inert towards the reaction compounds and the products thereof; and
   (c) drying said combined carrier and aqueous solution at a temperature which does not exceed the boiling point of water in said solution;
whereby said composition possesses superior storage stability relative to compositions comprised solely of hexamethylene-tetramine thiocyanate.

2. The composition according to claim 1 wherein said drying is achieved by spray drying.

3. The composition according to claim 1 wherein said carrier substance is selected from the group consisting of a polysaccharide selected from the group consisting of starch, cellulose, microcrystalline cellulose, carboxymethly cellulose and derivatives thereof; a dry product from milk selected from the group consisting of dried skim milk, whey powder and partially delactosed, demineralized or protein enriched whey powder; casein; a caseinate; lactose; silicic acid; silica; a polymeric salt of silicic acid and aluminum hydroxide.

4. A composition according to claim 1 wherein said carrier substance is genuine starch.

5. A composition according to claim 1 wherein said thiocyanate is potassium thiocyanate.

6. A composition according to claim 1 wherein said acid is a mineral acid.

7. A composition according to claim 6 wherein said mineral acid is selected from the group consisting of hydrochloric acid, phosphoric acid and sulfuric acid.

8. A composition according to claim 7 wherein said mineral acid is phosphoric acid.

9. A composition according to claim 1 wherein said acid is an organic acid.

10. A composition according to claim 9 wherein said organic acid is selected from the group consisting of lactic, citric, acetic and propionic acids.

11. A composition according to claim 9 wherein said organic acid is whey or a derivative thereof acidified by contact with a cation exchange resin in the acid form.

12. A dry stable bactericidal and mycocidal composition comprised of (1) the unisolated reaction product of hexamethylenetetramine with an alkali or alkaline earth metal thiocyanate in the aqueous phase in the presence of acid and (2) a physiologically harmless carrier substance substantially inert towards the reaction compounds and the products thereof; wherein said composition is prepared by a process comprising:
(a) reacting hexamethylenetetramine with and alkali or alkaline earth metal thiocyanate in the aqueous phase in the presence of acid at a pH no less than about 5.0;
(b) combining the aqueous solution product obtained in said reaction, without isolation of reaction product, with a physiologically harmless carrier substance substantially inert towards the reaction compounds and the products thereof in an amount such that the ultimate dry composition contains from about 10 to about 60% by weight carrier; and
(c) drying said combined carrier and aqueous solution at a temperature which does not exceed the boiling point of water in said solution, whereby the composition possesses superior storage stability relative to compositions comprised solely of hexamethylenetetramine thiocyanate.

13. A dry stable bactericidal and mycocidal composition comprised of (1) the unisolated reaction product of hexamethylenetetramine with an alkali or alkaline earth metal thiocyanate in the aqueous phase in the presence of acid and (2) a physiologically harmless carrier substance substantially inert towards the reaction compounds and the products thereof; wherein said composition is prepared by a process comprising:
(a) reacting hexamethylenetetramine with an alkali ar alkaline earth metal thiocyanate in the aqueous phase in the presence of acid at a pH no less than about 5.0, wherein the molar ratio of hexamethylenetetramine to said thiocyanate is in the range of from about 0.8:1 to about 1.5:1 and the molar ratio of acid to said thiocyanate is in the range of from about 0.9:1 to about 1.1:1;
(b) combining the aqueous solution product obtained in said reaction, without isolation of reaction product, with a physiologically harmless carrier substance substantially inert towards the reaction compounds and the products thereof in an amount such that the ultimate dry composition contains from about 10 to about 60% by weight carrier; and
(c) drying said combined carrier and aqueous solution at a temperature which does not exceed the boiling point of water in said solution;

whereby said composition possesses superior storage stability relative to compositions comprised solely of hexamethylenetetramine thiocyanate.

14. A method of combatting bacterial and mycotic infections in animals comprising administering an effective amount of the composition of claim 1 to said animals.

15. A method of preventing and diminishing yeast and molds in animal feedstuffs comprising adding to said feedstuff an effective amount of the composition of claim 1.

* * * * *

UNITED STATES PATENT AND TRADEMARK OFFICE
CERTIFICATE OF CORRECTION

PATENT NO. : 4,188,386
DATED : February 12, 1980
INVENTOR(S) : Robert Engl et al.

It is certified that error appears in the above—identified patent and that said Letters Patent is hereby corrected as shown below:

Column 2, line 18, "Centrigrades" should read -- Centigrades --.

Column 3, line 3, after "exchange" should read -- resin --.

Signed and Sealed this

Twenty-eighth Day of July 1981

[SEAL]

Attest:

GERALD J. MOSSINGHOFF

Attesting Officer

Commissioner of Patents and Trademarks